United States Patent
Sato et al.

(10) Patent No.: US 11,698,366 B2
(45) Date of Patent: Jul. 11, 2023

(54) HUMAN TISSUE STEM CELL AND USE THEREOF

(71) Applicant: KEIO UNIVERSITY, Tokyo (JP)

(72) Inventors: Toshiro Sato, Tokyo (JP); Mariko Shimokawa, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 796 days.

(21) Appl. No.: 16/497,659

(22) PCT Filed: Mar. 27, 2018

(86) PCT No.: PCT/JP2018/012356
§ 371 (c)(1),
(2) Date: Sep. 25, 2019

(87) PCT Pub. No.: WO2018/181276
PCT Pub. Date: Oct. 4, 2018

(65) Prior Publication Data
US 2021/0102934 A1    Apr. 8, 2021

(30) Foreign Application Priority Data

Mar. 28, 2017    (JP) ................................. 2017-063171

(51) Int. Cl.
| | |
|---|---|
| G01N 33/50 | (2006.01) |
| C07K 14/705 | (2006.01) |
| C12N 5/095 | (2010.01) |
| C12N 5/10 | (2006.01) |
| C12N 15/65 | (2006.01) |
| C12Q 1/6897 | (2018.01) |
| G01N 33/574 | (2006.01) |

(52) U.S. Cl.
CPC ........ *G01N 33/5011* (2013.01); *C07K 14/705* (2013.01); *C12N 5/0695* (2013.01); *C12N 5/10* (2013.01); *C12N 15/65* (2013.01); *C12Q 1/6897* (2013.01); *G01N 33/574* (2013.01)

(58) Field of Classification Search
None
See application file for complete search history.

(56) References Cited

U.S. PATENT DOCUMENTS

2010/0275280 A1    10/2010    Clevers et al.

FOREIGN PATENT DOCUMENTS

| | | |
|---|---|---|
| CN | 104593512 A | 5/2015 |
| CN | 110198741 A | 9/2019 |
| JP | 2005-528115 A | 9/2005 |
| JP | A-2015-173601 | 10/2015 |
| JP | 2016-028569 A | 3/2016 |
| WO | WO 2003/102215 A2 | 12/2003 |
| WO | WO 2009/142271 A1 | 11/2009 |
| WO | WO 2013/062083 A1 | 5/2013 |

OTHER PUBLICATIONS

Shimokawa et al., "Visualization of cancer stem cell and analysis of genetic cell lineage using human colorectal cancer organoid", Regenerative Medicine, Special Issue, 2015, vol. 14. p. 278, 0-62-5 (with English Translation) (Year: 2015).*
Barker, Nick, et al. "Identification of stem cells in small intestine and colon by marker gene Lgr5." Nature 449.7165 (2007): 1003-1007. (Year: 2007).*
Osawa, Hideki, et al. "Full-length LGR5-positive cells have chemoresistant characteristics in colorectal cancer." British journal of cancer 114.11 (2016): 1251-1260. (Year: 2016).*
Koo, Bon-Kyoung, and Hans Clevers. "Stem cells marked by the R-spondin receptor LGR5." Gastroenterology 147.2 (2014): 289-302. (Year: 2014).*
Irion, Stefan, et al. "Identification and targeting of the ROSA26 locus in human embryonic stem cells." Nature biotechnology 25.12 (2007): 1477-1482. (Year: 2007).*
Kreso A., et al., Evolution of the cancer stem cell model. Cell Stem Cell, 4 (14), 275-291, 2014.
Fujii M., et al., Nature Protocols, vol. 10, 1474-1485, 2015.
Mihara E., et al., eLIFE, vol. 5, e11621, 2016.
Fujii M., et al., Cell Stem Cell, vol. 18, 827-838, 2016.
Shimokawa, M. et al., "Visualization and targeting of LGR5+ human colon cancer stem cells", Nature [online], vol. 545, pp. 187 to 192, Epub Mar. 29, 2017, [retrieved on Jun. 11, 2018], <URL=https://www.nature.com/articles/nature22081>.
Shimokawa, M et al., "Visualization of cancer stem cell and analysis of genetic cell lineage using human colorectal cancer organoid", Regenerative Medicine, Special Issue, 2015, vol. 14. p. 278, 0-62-5.
International Search Report in PCT Application No. PCT/JP2018/012356, dated Jun. 19, 2018 (4 pages).
Barese et al., "Contributions of Gene Marking to Cell and Gene Therapies", Human Gene Therapy, Jun. 2011, 22: 659-668.
Bressan et al., "Efficient CRISPR/Cas9-assisted gene targeting enables rapid and precise genetic manipulation of mammalian neural stem cells", Development, 2017, 144: 635-648.
European Search Report for European Patent Application No. 18775344.7, dated Nov. 16, 2020, 5 pages.
Japanese Office Action for Japanese Application No. 2019-509868, dated Aug. 30, 2022.
Chinese Office Action for CN Application No. 201880020841.5, dated Nov. 8, 2022.
Kobayashi et al., "LGR5-Positive Colon Cancer Stem Cells Interconvert with Drug-Resistant LGR5-Negative Cells and Are Capable of Tumor Reconstitution", Stem Cells 30(12):2631-2644 (2012).

* cited by examiner

*Primary Examiner* — Robert J Yamasaki
(74) *Attorney, Agent, or Firm* — Lathrop GPM LLP; Brian C. Trinque

(57) ABSTRACT

A human tissue stem cell in which a gene of interest is introduced into a gene locus of a stem cell marker gene.

4 Claims, 5 Drawing Sheets

US 11,698,366 B2

HUMAN TISSUE STEM CELL AND USE THEREOF

TECHNICAL FIELD

The present invention relates to a human tissue stem cell and use thereof. More specifically, the present invention relates to a human tissue stem cell, a method of introducing a gene of interest into a gene locus of a stem cell marker gene of a human tissue stem cell, a method of testing whether or not a human tissue stein cell is a stem cell, a method of screening an anticancer drug effective against a cancer stem cell, and a method of testing the effectiveness of an anticancer drug against a cancer stem cell and a cancer cell.

Priority is claimed on Japanese Patent Application No. 2017-063171, filed on Mar. 28, 2017, the content of which is incorporated herein by reference.

BACKGROUND ART

A cancer stem cell theory focuses on a subpopulation of cancer cells that support tumor growth and self-replication (see, for example, NPL 1). According to the cancer stem cell theory, it is considered that a small number of cancer stem cells exist in tumor tissue from an early stage of carcinogenesis and tumor tissue is formed by repeated self-replication and differentiation of the cancer stem cells.

CITATION LIST

Non-Patent Literature

[NPL 1] Kreso A. and Dick J. E., Evolution of the cancer stem cell model. Cell Stem Cell, 4 (14), 275-291, 2014.

DISCLOSURE OF INVENTION

Technical Problem

However, a technique of performing gene locus-specific gene manipulation on stem cells such as cancer stein cells has not been established. Therefore, in particular, it was difficult to analyze human tissue stem cells in a cell lineage and to confirm that a single cell has self-replicating ability and differentiation ability. Thus, an object of the present invention is to provide a technique of performing gene locus-specific gene manipulation on tissue stem cells.

Solution to Problem

The present invention includes the following aspects.

[1] A human tissue stem cell in which a gene of interest is introduced into a gene locus of a stem cell marker gene.

[2] The human tissue stem cell according to [1], in which the stem cell marker gene is a Leucine-Rich Repeat-Containing G Protein-Coupled Receptor 5 (LGR5) gene.

[3] The human tissue stem cell according to [2], in which the gene of interest is introduced into exon 18 of an Lgr5 gene locus.

[4] The human tissue stem cell according to [1] or [2], in which the gene of interest is a reporter gene.

[5] The human tissue stem cell according to any one of [1] to [4], in which the gene of interest is a first reporter gene, and a second reporter gene that is operated by a forced expression promoter is further introduced.

[6] The human tissue stem cell according to any one of [1] to [5], which is a stem cell derived from cancer tissue.

[7] A method of introducing a gene of interest into a gene locus of a stem cell marker gene of a human tissue stem cell, the method including:

a step of introducing the gene of interest into the gene locus of the stem cell marker gene of a cultured organoid containing the human tissue stem cell by genome editing.

[8] The method according to [7], in which the step of introducing the gene of interest is performed by electroporation, and the method further includes a step of culturing the cultured organoid at 30° C. for 2 days, after introducing the gene of interest.

[9] The method according to [7] or [8], in which the gene locus of the stem cell marker gene is an Lgr5 gene locus.

[10] The method according to [9], in which the gene of interest is introduced into exon 18 of the Lgr5 gene locus.

[11] The method according to any one of [7] to [10], in which the gene of interest is a gene encoding a cell lineage marker-inducing protein.

[12] A method of testing whether or not a human tissue stem cell prepared by the method according to [11] is a stem cell, including:

a step of detecting self-replication and differentiation of the human tissue stem cell by performing cell lineage analysis on the human tissue stem cell, in which detection of both self-replication and differentiation of the human tissue stem cell indicates that the human tissue stem cell is a stem cell.

[13] The method according to any one of [7] to [12], in which the human tissue stem cell is a stem cell derived from cancer tissue.

[14] A method of screening an anticancer drug effective against a cancer stein cell, including:

a step of culturing a cancer stem cell into which a reporter gene that is operated by a promoter of a cancer stein cell marker gene is introduced, in the presence of a substance to be tested; and a step of measuring an expression level of the reporter gene, in which a decrease in the expression level of the reporter gene indicates that the substance to be tested is the anticancer drug effective against the cancer stem cell.

[15] A method of testing the effectiveness of an anticancer drug against a cancer stem cell and a cancer cell, including:

a step of culturing a cancer stem cell into which a first reporter gene that is operated by a promoter of a cancer stem cell marker gene and a second reporter gene that is operated by a forced expression promoter are introduced, in the presence of the anticancer drug; and a step of measuring an expression level of each of the first and second reporter genes, in which a decrease in the expression level of the first reporter gene indicates that the anticancer drug is an anticancer drug effective against the cancer stem cell, and a decrease in the expression level of the second reporter gene indicates that the anticancer drug is an anticancer drug effective against the cancer stem cell and the cancer cell.

The present invention can also include the following aspects.

[P1] A tissue stem cell in which a gene of interest is introduced into a gene of interest locus.

[P2] The tissue stem cell according to [P1], in which the gene of interest locus is a gene locus of a stem cell marker gene.

[P3] The tissue stem cell according to [P2], in which the stem cell marker gene is a Leucine-Rich Repeat-Containing G Protein-Coupled Receptor 5 (LGR5) gene.

[P4] The tissue stem cell according to [P3], in which the gene of interest is a reporter gene.

[P5] The tissue stem cell according to any one of [P1] to [P4], in which the gene of interest is a first reporter gene, and a second reporter gene that is operated by a forced expression promoter is further introduced.

[P6] The tissue stem cell according to any one of [P1] to [P5], which is a stem cell derived from cancer tissue.

[P7] A method of introducing a gene of interest into a gene of interest locus of a tissue stem cell, including:

a step of introducing the gene of interest into the gene of interest locus of a cultured organoid containing the tissue stem cell.

[P8] The method according to [P7], in which the step of introducing the gene of interest is performed by electroporation, and the method further includes a step of culturing the cultured organoid at 30° C. for 2 days, after introducing the gene of interest.

[P9] The method according to [7] or [8], in which the gene of interest locus is a gene locus of a stem cell marker.

[P10] The method according to [P9], in which the gene of interest is a gene encoding a cell lineage marker-inducing protein.

[P11] A method of testing whether or not a tissue stem cell prepared by the method according to [P10] is a stem cell, including:

a step of detecting self-replication and differentiation of the tissue stem cell by performing cell lineage analysis on the tissue stem cell, in which detection of both self-replication and differentiation of the tissue stem cell indicates that the tissue stem cell is a stem cell.

[P12] The method according to any one of [P7] to [P11], in which the tissue stem cell is a stem cell derived from cancer tissue.

[P13] A method of screening an anticancer drug effective against a cancer stem cell, including:

a step of culturing a cancer stem cell into which a reporter gene that is operated by a promoter of a cancer stem cell marker gene is introduced, in the presence of a substance to be tested; and a step of measuring an expression level of the reporter gene, in which a decrease in the expression level of the reporter gene indicates that the substance to be tested is the anticancer drug effective against the cancer stem cell.

[P14] A method of testing the effectiveness of an anticancer drug against a cancer stem cell and a cancer cell, including:

a step of culturing a cancer stem cell into which a first reporter gene that is operated by a promoter of a cancer stem cell marker gene and a second reporter gene that is operated by a forced expression promoter are introduced, in the presence of the anticancer drug; and a step of measuring an expression level of each of the first and second reporter genes, in which a decrease in the expression level of the first reporter gene indicates that the anticancer drug is an anticancer drug effective against the cancer stem cell, and a decrease in the expression level of the second reporter gene indicates that the anticancer drug is an anticancer drug effective against the cancer stem cell and the cancer cell.

Advantageous Effects of Invention

According to the present invention, it is possible to provide a technique of performing gene locus-specific gene manipulation on a tissue stem cell.

BEST MODE FOR CARRYING OUT THE INVENTION

[Tissue Stem Cell]

Figure 1:
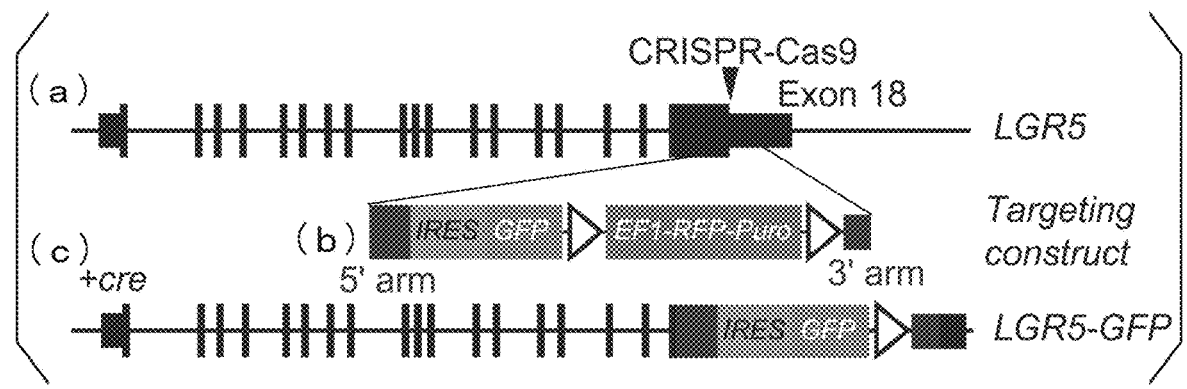
FIG. 1(a) is a schematic diagram of a human LGR5 gene locus.
FIG. 1(b) is a schematic diagram showing a structure of a targeting construct prepared in Experimental Example 1.
FIG. 1(c) is a schematic diagram showing a structure of the LGR5 gene locus of an organoid prepared in Experimental Example 1.

According to an embodiment of the present invention, a tissue stem cell is provided in which a gene of interest is introduced into a gene of interest locus.

In the present embodiment, the tissue stem cell may be a human cell or a non-human animal cell. The stem cell is a cell having self-replicating ability and differentiation ability. The tissue stem cell is a stem cell that exists in tissue, also called a somatic stem cell, and is different from an embryonic stem cell (ES cell) or an induced pluripotent stem cell (iPS cell). In the present specification, the tissue stem cell includes a cancer stem cell. In addition, the tissue stem cell of the present embodiment is assumed to include a cell that can dedifferentiate into a stem cell due to cell plasticity.

In the related art, it was difficult to perform gene locus-specific gene manipulation on a tissue stem cell. On the other hand, as described later in Examples, the inventors clarified that a tissue stem cell in which a gene of interest is introduced into a gene of interest locus can be prepared by performing gene locus-specific gene manipulation on a cultured organoid containing a tissue stem cell.

In the tissue stem cell of the present embodiment, the gene of interest locus may be any gene locus of interest, for example, it may be a gene locus of a stem cell marker gene. In more detail, the tissue stem cell of the present embodiment may be a cancer stem cell, and the gene of interest locus may be a gene locus of a cancer stein cell marker gene. Examples of the cancer stem cell marker gene include LGR5, SPARC Related Modular Calcium Binding 2 (SMOC2), Repulsive Guidance Molecule Family Member B (RGMB), AXIN2, Olfactomedin 4 (OLFM4), Cell Division Cycle Associated 7 (CDCA7), Leucine Rich Repeats And Immunoglobulin Like Domains 1 (LRIG1), Ring Finger Protein 43 (RNF43), and Achaete-Scute Family BHLH Transcription Factor 2 (ASCL2), but are not limited thereto.

In addition, cancer derived from the cancer stem cell is not particularly limited, and for example, the cancer stein cell may include a cancer stem cell of colon cancer, gastric cancer, or pancreatic cancer. The inventors confirmed that, in these cancer stem cells, an LGR5 gene can be used as a cancer stem cell marker.

In addition, the inventors clarified that a gene of interest can be introduced into a gene of interest locus of a tissue stem cell of a normal cell by performing gene locus-specific gene manipulation on a cultured organoid derived from a normal cell.

Whether it is the cultured organoid derived from a normal cell or the cultured organoid derived from the cancer cell can be determined by requirement of a growth factor necessary for culturing the organoid, confirmation of gene mutation by sequencing, confirmation of chromosomal abnormality, and the like.

In addition, in the stem cell of the present embodiment, the gene of interest may be any gene. For example, the gene of interest may also be a reporter gene. Also, the reporter gene may be introduced into a region other than exon 1 of a gene located at the gene of interest locus. For example, the reporter gene may be introduced into exon 18 of the LGR5 gene. The reporter gene is not particularly limited, and examples thereof include various fluorescent proteins and enzymes.

In gene locus-specific gene manipulation by genome editing and the like, the gene of interest is introduced into the exon 1 of a target gene. The inventors first attempted to introduce the reporter gene into exon 1 of the LGR5 gene of a colon cancer stem cell. However, this gene introduction could not be easily performed. On the other hand, as described later in Examples, when the reporter gene was introduced into exon 18 of the LG5 gene, desired gene introduction could be performed efficiently.

The gene of interest to be introduced into the gene of interest locus need not have a promoter sequence. That is, the gene of interest may be configured to be expressed by a promoter at the gene of interest locus.

For example, the gene of interest can be expressed by the promoter at the locus of interest, by linking an internal ribosomal entry site (IRES), a ribosomal skip site such as T2A or P2A, or the like to a 5' side of the gene of interest.

The tissue stem cell of the present embodiment may be a cancer stem cell in which a second reporter gene that is operated by the forced expression promoter is introduced, in addition to a first reporter gene that is introduced into the gene locus of the cancer stem cell marker gene and is operated by the promoter of the marker gene. The second reporter gene need not be introduced specifically to the gene locus. In addition, as the forced expression promoter, a promoter usually used for forced expression of a gene in an animal cell can be used, and examples thereof include CMV promoter and EF1α promoter but are not limited thereto.

The first reporter gene and the second reporter gene are preferably distinguishable from each other. For example, the first reporter gene and the second reporter gene may be genes encoding fluorescent proteins that emit fluorescence having different wavelengths from each other.

The first reporter gene is expressed when the cancer stem cell marker gene is expressed, that is, when the cell maintains a cancer stem cell property. On the other hand, the second reporter gene is expressed regardless of the expression of the cancer stem cell marker gene, that is, both when the cancer stem cell maintains the cancer stem cell property and when the cancer stem cell loses the cancer stein cell property is lost. Therefore, the expression of the first reporter gene indicates the presence of the cancer stem cell, and the expression of the second reporter gene indicates both the presence of the cancer stem cell and the presence of the cancer cell. The term cancer cell refers to a cancer cell that does not express a cancer stem cell marker gene.

As described later in Examples, an effect on the cancer stem cell and the cancer cell can be distinguished and evaluated by culturing the cancer stem cell in the presence of a substance to be tested and measuring an expression level of each of the first reporter and the second reporter genes. Therefore, the cancer stem cell can be used for screening of an anticancer drug and the like effective against the cancer stem cell.

[Method of Introducing Gene of Interest into Gene of Interest Locus of Tissue Stem Cell]

According to an embodiment of the present invention, a method is provided for introducing a gene of interest into a gene of interest locus of a tissue stem cell, including: a step of introducing the gene of interest into the gene of interest locus of a cultured organoid containing the tissue stem cell. The method of the present embodiment can be a method including a step of introducing the gene of interest into the gene of interest locus of cells forming the cultured organoid.

In the method of the present embodiment, the stem cell is the same as those described above, and examples thereof include a cancer stem cell and a somatic stem cell.

In the related art, it was difficult to perform gene manipulation on a stem cell such as a cancer stem cell and a tissue stem cell. In particular, it was difficult to perform gene locus-specific gene manipulation on a tissue stem cell. On the other hand, as described later in Examples, the inventors clarified that a cultured organoid into which the gene of interest is introduced can be prepared by performing gene modification of a gene of a cultured organoid containing the tissue stem cell.

In addition, as described later in Examples, according to the present embodiment, it is possible to perform gene locus-specific gene manipulation on the tissue stem cell. Accordingly, a tissue stem cell in which a gene of interest is introduced into the gene of interest locus can be prepared.

In the present specification, the term organoid means organ-like tissue obtained by three-dimensional culture of a cell. In addition, in the present specification, a cell mass is also included in the organoid. The method for three-dimensional culture is not particularly limited, and examples thereof include a method using Matrigel, a method using collagen, and a method using laminin.

In the method of the present embodiment, the cultured organoid is not particularly limited as long as it is an organoid including a tissue stem cell, and examples thereof include an epithelial organoid cell, an epithelial tumor cell organoids, and the like. In addition, examples of the epithelial cell include a gastrointestinal epithelial cell of the stomach, small intestine, large intestine, bile duct, pancreatic duct epithelium, and the like, and epithelial cells of tissue other than digestive organs such as the breast and prostate.

As a method of culturing the organoid, a known culturing method can be used. In particular, in the method of culturing a stem cell derived from cancer tissue, it is possible to select a culturing method optimized individually for each cancer tissue (for example, see Fujii M., et al., Nature Protocols, Vol. 10, 1474-1485, 2015; Mihara E., et al., eLIFE, Vol. 5, E11621, 2016; Fujii M., et al., Cell Stem Cell, Vol. 18, 827-838, 2016).

In the method of the present embodiment, as the step of introducing the gene of interest into the cultured organoid, a known gene introduction method can be used. In particular, as shown in Examples, it is preferable to perform the introduction by electroporation. Furthermore, after the electroporation, the method preferably includes a step of culturing the cultured organoid at 30° C. for 2 days. The inventors clarified that the efficiency of gene introduction into an organoid can be significantly improved by providing such a step.

[Method of Testing Whether Tissue Stem Cell is Stem Cell]

According to an embodiment of the present invention, a method is provided for testing whether or not the tissue stem cell marked with a cell lineage marker that is operated by the promoter of the target gene is a stem cell, the method including a step of detecting self-replication and differentiation of the tissue stem cell by performing cell lineage analysis on the tissue stem cell, in which detection of both self-replication and differentiation of the tissue stem cell indicates that the tissue stem cell is a stem cell. The cell lineage marker will be described later.

The method of the present embodiment is a method of proving that a cell considered to be a tissue stem cell is a stem cell. In addition, the method of the present embodiment is a method of testing whether or not the target gene is a stein cell marker. That is, the method of the present embodiment is a method of testing whether or not the target gene is a stem cell marker, the method including a step of culturing a cell marked with a cell lineage marker that is operated by a promoter of the target gene; and a step of detecting self-replication and differentiation of the cell by performing cell lineage analysis on the cell, in which detection of both self-replication and differentiation of the cell indicates that the target gene is a stem cell marker.

A stem cell is a cell having self-replicating ability and differentiation ability. Therefore, in order to prove that the target cell is a stem cell, it is necessary to show that one target cell performs both self-replication and differentiation. Alternatively, in order to prove that the target gene is a stem cell marker, it is necessary to show that a single cell expressing the target gene performs both self-replication and differentiation.

In order to show that a single cell performs both self-replication and differentiation, it is necessary to show that a cell derived from a single cell performs both self-replication and differentiation, by performing cell lineage analysis that tracks and observes cells derived from a single cell. Cell lineage analysis is an analysis method that identifies and tracks a cell that is a progeny of a single cell of a target, regardless of whether or not the single cell of the target repeats cell division or differentiates and changes a property thereof.

In the present specification, a cell lineage marker refers to a marking that can identify that a given cell is the progeny of a single cell of interest, even if the single cell of interest repeats cell division or differentiates and changes a property thereof.

In the method of the present embodiment, a cell expressing the target gene is marked with a cell lineage marker so as to be operated by the promoter of the target gene. As a result, it is possible to identify and observe a cell that expresses the target gene and a progeny thereof. As a result, when it is confirmed that the marked cell performed both self-replication and differentiation, the target gene can be proven to be a stem cell marker. The cell lineage marker is preferably operated by the promoter of the target gene at the target gene locus.

The cell lineage marker is not particularly limited as long as the cell can be marked such that the progeny thereof can be traced. For example, a cell lineage marker-inducing protein expressed by the promoter of the target gene and a cell lineage marker construct which is introduced into a cell separately therefrom can be used in combination. The cell lineage marker-inducing protein acts on the cell lineage marker construct to mark the cell in a cell lineage-specific manner.

As a more specific cell lineage marker, for example, variants of a Cre-LoxP system such as a Cre-loxP system, a VCre-VLoxP system, and an SCre-SloxP system can be used; an Flp-Frt system using a recombinant enzyme derived from *Saccharomyces cerevisiae* can be used; and these can be used in combination.

Examples of the cell lineage marker-inducing protein include Cre recombinase, VCre recombinase, SCre recombinase, and Hp recombinase.

As the cell lineage marker construct, for example, a cell lineage marker construct can be used that can perform marking of the cell lineage by the cell lineage marker-inducing protein used. For example, when the cell lineage marker-inducing protein is the Cre recombinase, a construct that has a loxP sequence and can be detected when gene recombination occurs can be used. The cell lineage marker construct may be configured, for example, so as to express a fluorescent protein when gene recombination occurs.

According to this system, gene recombination occurs when the target gene has been expressed, and then the cell expresses, for example, a fluorescent protein. Since the cell expresses a fluorescent protein even when divided, it is possible to perform cell lineage analysis.

In the method of the present embodiment, a tissue stem cell into which the cell lineage marker-inducing protein is introduced so as to be operated by the promoter of the target gene can be prepared by the method described above. On the other hand, the cell lineage marker construct need not be introduced specifically to the gene locus.

In the related art, it was difficult to perform gene locus-specific gene manipulation on a tissue stem cell. Therefore, it was difficult to introduce the cell lineage marker-inducing protein into the tissue stem cell so as to be operated by the promoter of the target gene. However, as described above, the inventors clarified that it is possible to perform gene locus-specific gene manipulation on tissue stem cells by introducing a gene into a cultured organoid.

As a result, it is possible to mark the tissue stem cell with a cell lineage marker by introducing a cell lineage marker-inducing protein so as to be operated by the promoter of the target gene and introducing the cell lineage marker construct separately therefrom to the tissue stem cell, and it is possible to test whether or not a target gene is a stem cell marker.

[Method of Screening Anticancer Drug Effective Against Cancer Stem Cell]

According to an embodiment of the present invention, a method is provided for screening an anticancer drug effective against a cancer stem cell, including: a step of culturing a cancer stem cell into which a reporter gene that is operated by a promoter of a cancer stem cell marker gene is introduced, in the presence of a substance to be tested; and a step of measuring an expression level of a reporter gene, in which a decrease in the expression level of the reporter gene indicates that the substance to be tested is an anticancer drug effective against cancer stem cells.

In the screening method of the present embodiment, the cancer stem cell may be cultured in a form of an organoid containing the cancer stem cell. In addition, the cancer stem cell is preferably a cancer stem cell that has been proven to be a cancer stem cell by the method described above. That is, the cancer stem cell marker gene is preferably a cancer stem cell that has been proven to be a cancer stem cell marker by the method described above.

In addition, the reporter gene is not particularly limited, and examples thereof include various fluorescent proteins and enzymes. The reporter gene is preferably operated by the promoter at the gene locus of the cancer stem cell marker gene.

As described later in Examples, an effect of the substance to be tested on the cancer stem cell can be measured by the screening method of the present embodiment. As a result, it is possible to screen the anticancer drug effective against the cancer stem cell. The substance to be tested is not particularly limited, and examples thereof include a compound library and a library of existing drugs including an antibody drug.

According to another embodiment of the present invention, a method is provided for testing the effectiveness of an anticancer drug against a cancer stem cell and a cancer cell, including: a step of culturing a cancer stem cell into which a first reporter gene that is operated by a promoter of a cancer stem cell marker gene and a second reporter gene that is operated by a forced expression promoter are introduced, in the presence of the anticancer drug; and a step of measuring an expression level of each of the first and second reporter genes, in which a decrease in the expression level of the first reporter gene indicates that the anticancer drug is an anticancer drug effective against the cancer stem cell, and a decrease in the expression level of the second reporter gene indicates that the anticancer drug is an anticancer drug effective against the cancer stem cell and the cancer cell.

The method of the present embodiment is a method of screening an anticancer drug. As the forced expression promoter, a promoter usually used for forced expression of a gene in an animal cell can be used, and examples thereof include CMV promoter and EF1α promoter but are not limited thereto.

In the method of the present embodiment, the first reporter gene is preferably operated by the promoter at the gene locus of the cancer stem cell marker gene. In addition, the first reporter gene and the second reporter gene are preferably distinguishable from each other. For example, the first reporter gene and the second reporter gene may be genes encoding fluorescent proteins that emit fluorescence having different wavelengths from each other.

As described later in Examples, the effect of a target anticancer drug on the cancer stem cell and the cancer cell can be evaluated by the method of the present embodiment.

Accordingly, the method of the present embodiment can be used for screening an anticancer drug or the like effective against cancer stem cells.

EXAMPLES

Next, the present invention will be described in more detail with reference to Experimental Examples, but the present invention is not limited to the following Experimental Examples.

Experimental Example 1

(Introduction of Reporter Gene into LGR5 Gene Locus of Colon Cancer Stem Cell)

<<Preparation of Construct>>

CRISPR-Cas9 plasmid targeting exon 18 of an LGR5 gene was prepared by a general method. FIG. 1(*a*) is a schematic diagram of a human LGR5 gene locus. In addition, a targeting construct that introduces the reporter gene into exon 18 of the LGR5 gene was prepared. As the reporter gene, a gene encoding green fluorescent protein (GFP) was used. FIG. 1(*b*) is a schematic diagram showing a structure of the prepared targeting construct.

The targeting construct was prepared by linking 5' and 3' arms each having a length of 1 kbp to the IRES-GFP-loxP-EF1-RFP-T2A-Puro-loxP plasmid (model "HR180PA-1", System Bioscience).

<<Culture of Organoid>>

An experiment was conducted with approval from the Ethics Committee of Keio University School of Medicine. Colon cancer tissue excised from a patient was cut into small fragments and washed at least 10 times with ice-cold phosphate buffer (PBS). Subsequently, Liberase (model "TH", Roche Life Sciences) was added thereto, and was digested at 37° C. for 60 minutes with vigorous pipetting every 15 minutes. Subsequently, the remaining fragment was further digested using an enzyme (type "TrypLE Express", Invitrogen) at 37° C. for 20 minutes.

Subsequently, the supernatant was collected and centrifuged at 4° C. and 200×g for 3 minutes. Subsequently, the precipitate was suspended in Matrigel (BD Bioscience) and dispensed into 24-well plates each to have 25 μL/well. Subsequently, a medium was added after Matrigel was polymerized.

As the medium, a medium in which penicillin, streptomycin, 10 mM HEPES, 2 mM GlutaMAX (Thermo Fisher Scientific), 1×B27 (Life Technologies), 10 nM gastrin I (Sigma), and 1 mM N-acetylcysteine (Wako Pure Chemical Industries) were added to a Dulbecco's-modified Eagle/F12 medium was used as a basic medium. In addition, in some cases, 50 ng/mL mouse recombinant EGF, 100 ng/mL mouse recombinant Noggin, and 500 nM A83-01 (Tocris) was added to the medium.

The inventors previously clarified that a colon cancer organoid can be cultured for a long period of time by the culturing method described above and the colon cancer organoid contains a colon cancer stem cell.

<<Gene Introduction>>

A gene was introduced into the cultured organoid by an electroporation method. After the gene introduction, the cultured organoid was cultured at 30° C. for 2 days. Subsequently, 3 days after the gene introduction, selective culture was performed in the presence of 2 μg/mL puromycin for 3 days.

Subsequently, drug-resistant organoid clones were selected and propagated individually. Genomic DNA was extracted from each organoid clone, and it was confirmed by PCR and Southern blotting that a gene of interest had been introduced.

Subsequently, the RFP-T2A-Puro selection cassette flanked by loxP sequence was removed by being transiently infected with an adenovirus expressing Cre recombinase. Subsequently, RFP-negative organoids were selected and cloned. Subsequently, it was confirmed by the PCR that the RFP-T2A-Puro selection cassette was removed.

Using the above method, organoids of 3 clones named CRC7, CRC12, and CRC28 were obtained. FIG. 1(c) is a schematic diagram showing a structure of the LGR5 gene locus of the obtained organoid. Hereinafter, these organoids may be referred to as "LGR5-GFP organoids" in some cases.

Experimental Example 2

(Confirmation of Stem Cell Hierarchy)
>>Organoid Xenograft>>
An animal experiment was conducted with approval from the Animal Experiment Committee of Keio University School of Medicine. The LGR5-GFP organoids of 3 clones prepared in Experimental Example 1 were each xenografted under renal capsules of immunodeficient mice. As the immunodeficient mice, NOD/Shi-scid IL-2Rγnull (NOG) mice (7 to 12 weeks old, male) were used.
>>Detection of Cancer Stem Cell and Differentiated Cancer Cell>>
A formed tumor was removed from each mouse and immediately fixed with 4% paraformaldehyde to prepare a frozen tissue section. Subsequently, GFP fluorescence indicating the presence of a cancer stem cell was detected in the prepared tissue section. In addition, Keratin 20 (KRT20) as a differentiation marker was detected by immunostaining.

Figure 2:
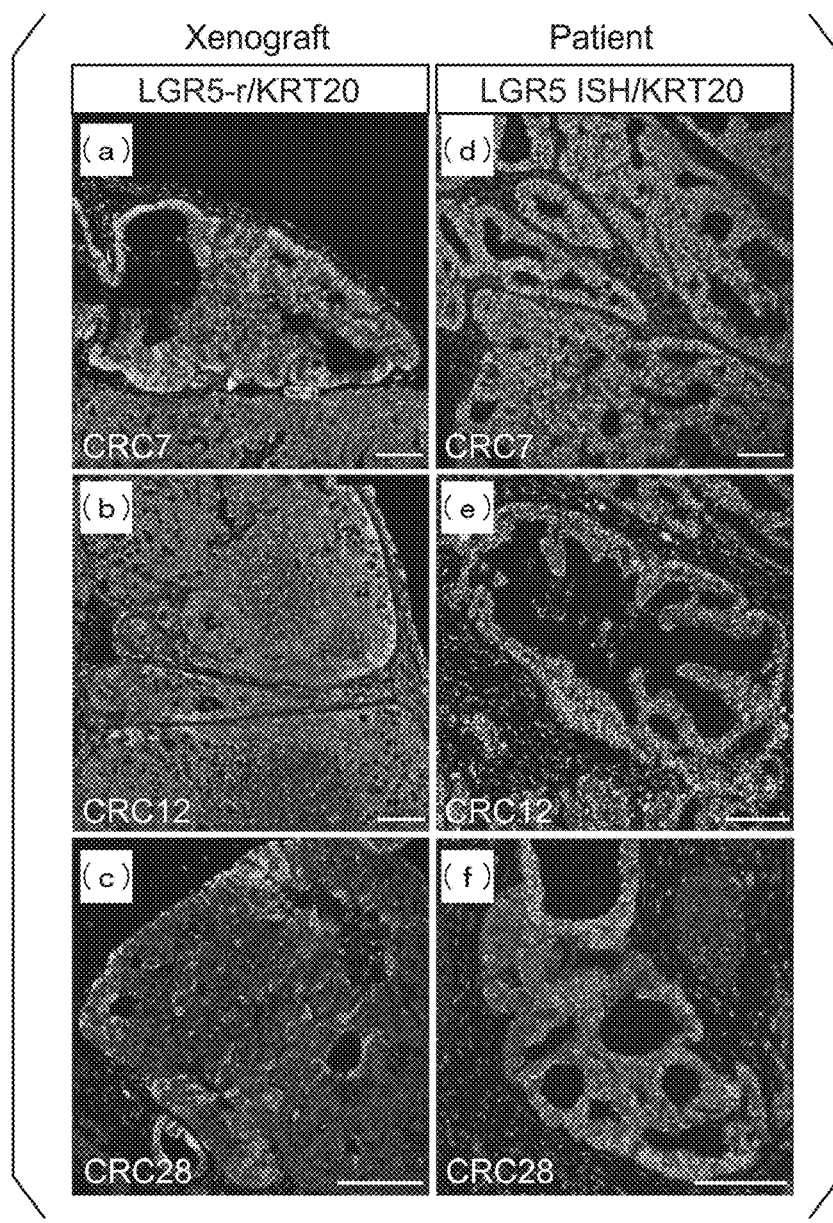
FIGS. 2(a) to 2(c) show fluorescence micrographs of a tissue section of tumor tissue derived from an organoid transplanted to a mouse in Experimental Example 2.
FIGS. 2(d) to 2(f) show fluorescence micrographs obtained by observing a section of colon cancer tissue derived from a patient from which an organoid clone was established, in Experimental Example 2.

FIGS. 2(a) to 2(c) show fluorescence micrographs of the tissue section of the tumor tissue derived from the transplanted organoid. In FIG. 2, "Xenograft" indicates the tumor tissue derived from the xenografted organoid, and "Patient" indicates tumor tissue derived from a patient to be described later. In addition, a scale bar indicates 100 μm. FIG. 2 (a) shows the result of the tumor tissue derived from clone CRC7 of LGR5-GFP organoid, FIG. 2 (b) shows the result of the tumor tissue derived from clone CRC12, and FIG. 2 (c) shows the result of the tumor tissue derived from clone CRC28.

As a result, it was clear that a GFP-positive cell (a cancer stem cell) was present in an outermost region of the tumor, and KRT20 (a differentiated cell) was present inside the tumor.

In addition, FIGS. 2(d) to 2(f) show fluorescence micrographs of a result of detecting mRNA of LGR5 by in situ hybridization and detecting KRT20 by immunostaining in a section of the colon cancer tissue derived from the patient from which each organoid clone was established.

FIG. 2 (d) shows the result of the tumor tissue of the patient used to establish clone CRC7, FIG. 2 (e) shows the result of the tumor tissue of the patient used to establish clone CRC12, and FIG. 2 (f) shows the result of the tumor tissue of the patient used to establish clone CRC28.

As a result, also in the tumor tissue of the patient, it was clear that an LGR5-expressing cell (a cancer stem cell) was present in an outermost region of the tumor, and KRT20 (a differentiated cell) was present inside the tumor.

From the above results, it was confirmed that the stem cell hierarchy in the tumor tissue of the patient was reproduced in the tumor tissue derived from the organoid.

Experimental Example 3

(Proof that LGR5 Gene-Expressing Cell is a Cancer Stem Cell)
A cancer stem cell was marked with a cell lineage marker, and cell lineage analysis was performed to examine whether or not a single cell performs both self-replication and differentiation.
<<Marking with Cell Lineage Marker>>
First, a cancer stem cell was marked with a cell lineage marker so as to be operated by a promoter of the LGR5 gene. FIGS. 3(a) to 3(c) show diagrams illustrating marking with the cell lineage marker.

First, an IRES-CreER construct was introduced into the LGR5 gene locus of a cultured organoid derived from colon cancer by the same method as in Experimental Example 1. CreER protein is a recombinase that normally exists in cytoplasm, but moves into the nucleus by binding to tamoxifen and causes recombination with the loxP sequence to occur. FIG. 3(a) is a diagram showing a schematic diagram of a completed LGR5 gene locus.

Figure 3:
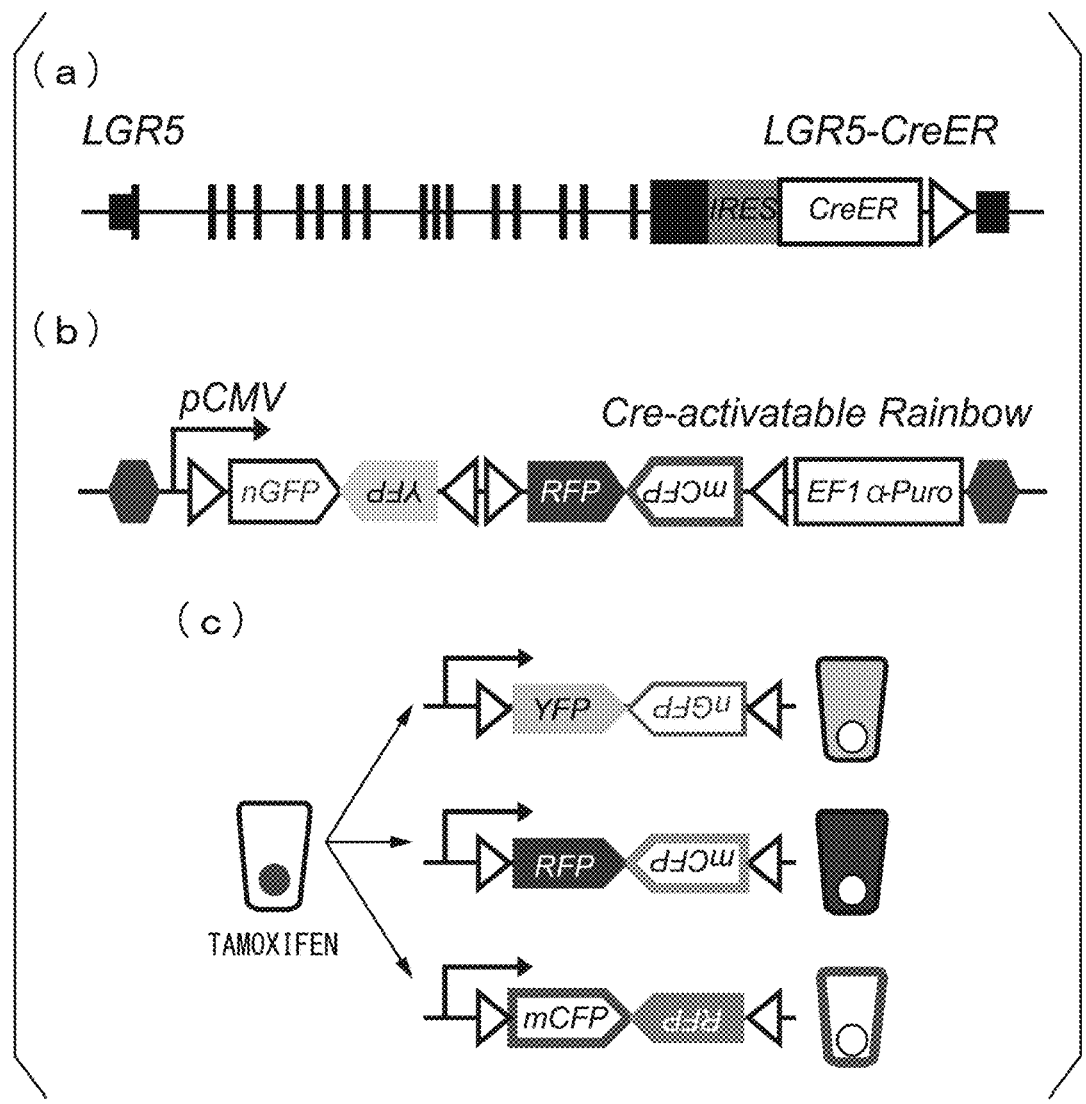
FIGS. 3(a) to 3(c) show diagrams illustrating marking by a cell lineage marker.

In addition, a reporter cassette was further introduced into the organoid into which IRES-CreER was introduced, by the same method as in Experimental Example 1. As the reporter cassette, a rainbow cassette cut out from CMV-Brainbow-2.1R plasmid (model "#18723", Addgene) was used. FIG. 3 (b) is a diagram showing a schematic diagram of the rainbow cassette.

The organoid marked with the cell lineage marker shown in FIGS. 3(a) and 3(b) will be described. A cancer stem cell present in the organoid marked with the cell lineage marker described above expresses the LGR5 gene and therefore express the CreER protein. In the absence of the tamoxifen, since the CreER was present in the cytoplasm, the recombination of the rainbow cassette did not occur. Therefore, nuclear GFP (nGFP) is expressed, and GFP fluorescence is observed in the nucleus.

When tamoxifen is administered to the cell, the CreER moves into the nucleus, and recombination occurs in random combinations in the multiple loxP sequences present in the rainbow cassette. As a result, for example, the gene sequence shown in FIG. 3 (c) is formed. As a result, in some cases, the cell may express any of yellow fluorescent protein (YFP), red fluorescent protein (RFP), and cyan fluorescent protein (mCFP).

A recombinant cell that once expresses any fluorescent protein and a progeny thereof continue to express the same fluorescent protein. Therefore, a cell derived from a single cell can be traced and analyzed. Hereinafter, the organoids marked with the cell lineage marker may be referred to as "LGR5-CreER/Rainbow organoid" in some cases.
<<Cell Lineage Analysis of Cancer Stem Cell>>
Cancer stem cells express the LGR5 gene. Therefore, the cancer stem cells contained in the LGR5-CreER/Rainbow organoid express CreER, and in the presence of tamoxifen change from cells emitting nGFP fluorescence to cells emitting YFP, RFP, and mCFP fluorescence.

Cell lineage analysis of the cancer stem cells was performed using this system. Specifically, first, the LGR5-CreER/Rainbow organoid was xenografted under the renal capsule of NOG mice (7-12 weeks old, male) by the same method as Experimental Example 2. Subsequently, one month after the transplantation, the tamoxifen was administered to mice. Specifically, a tumor was removed from each mouse 3 days after and 28 days after the administration of the tamoxifen, and immediately fixed with 4% paraformaldehyde to prepare a frozen tissue section.

Subsequently, fluorescence observation of the prepared tissue section, in situ hybridization of mRNA of the LGR5, and immunostaining of KRT20 were performed to observe a behavior of the cancer stem cell.

As a result, it was confirmed that immediately after the administration of tamoxifen, cancer stem cells were present in the outermost region of the tumor tissue. Thereafter, it was confirmed that the tumor tissue was continuously formed by the cell lineage-marked cell clone.

In addition, it was also found that a cell that initially expressed the LGR5 gene forms a clonal structure including an LGR5-positive cell and an LGR5-negative cell. In addition, it was confirmed that a cell that expressed the LGR5 gene did not initially express KRT20, but was differentiated into KRT20 positive cell 1 week after the administration of the tamoxifen.

From the above results, it was proven that in humans an LGR5-positive cell is a cancer stem cell and has self-replicating ability and differentiation ability over a long period of time. That is, it was proven that in humans the LGR5 gene is a cancer stem cell marker.

Experimental Example 4

(Examination of Effectiveness of Cancer Treatment Targeting Cancer Stem Cell)

A drug-induced suicide gene was incorporated into a cancer stem cell, and the effectiveness of cancer treatment targeting the cancer stem cell was examined.

<<Preparation of Cancer Stem Cells in which Drug-Induced Suicide Gene was Introduced>>

First, an IRES-iCaspase9-T2A-tdTomato construct was introduced into the LGR5 gene locus of the cultured organoid derived from colon cancer by the same method as in Experimental Example 1. Hereinafter, these organoids may be referred to as "LGR5-iCT organoids" in some cases.

iCaspase 9 is a drug-induced suicide gene. The iCaspase 9 has no activity in a monomer, but forms a dimer in the presence of AP20187 (dimerizer, APExBIO) to induce apoptosis. Also, TdTomato is a kind of red fluorescent protein (RFP).

Figure 4:
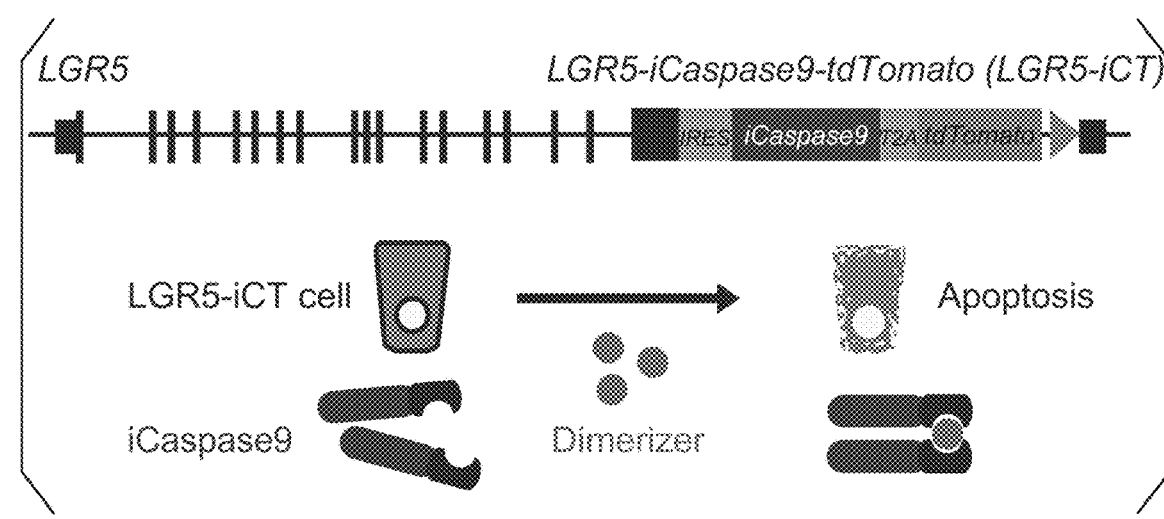
FIG. 4 is a diagram illustrating a structure of an LGR5 gene locus of an organoid prepared in Experimental Example 4 and behavior of a drug-induced suicide gene.

FIG. 4 is a diagram illustrating a structure of the completed LGR5 gene locus and behavior of the drug-induced suicide gene. In this system, the iCaspase and the tdTomato fluorescent protein are expressed by the promoter of the LGR5 gene. Therefore, it is possible to confirm the presence of the LGR5-positive cell by observing the fluorescence of the tdTomato. Then, in the presence of the AP20187, the LGR5-positive cell induces apoptosis and die. As a result, the fluorescence of the tdTomato becomes not observed.

<<Confirmation of Behavior of LGR5-iCT Organoid>>

The LGR5-iCT organoid was xenografted under the renal capsule of NOG mice (7-12 weeks old, male) by the same method as Experimental Example 2. Subsequently, after a tumor was formed, the AP20187 was administered to mice daily for 5 days. In addition, control mice to which only a solvent was administered daily for 5 days. Thereafter, a tumor size of each mouse was measured regularly.

Figure 5:
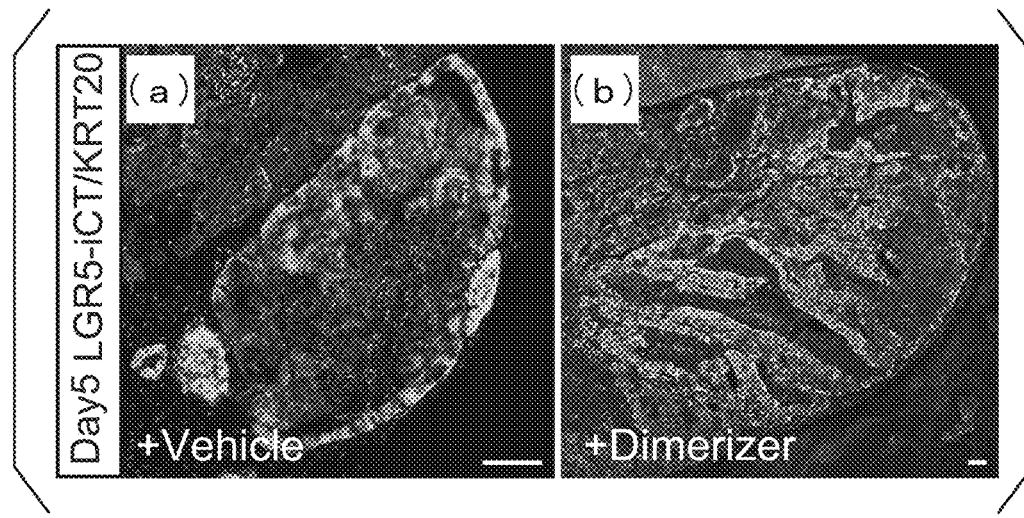
FIG. 5(a) is a fluorescence micrograph showing a result obtained by observing a section of tumor tissue of a control mouse in Experimental Example 4.
FIG. 5(b) is a fluorescence micrograph showing a result obtained by observing a section of tumor tissue of a mouse to which AP20187 is administered, in Experimental Example 4.

FIGS. 5 (a) and 5(b) show fluorescence micrographs of a result obtained by extracting a tumor of each mouse on the 5th day from the start of administration of the AP20187 to prepare a tissue section and detecting the fluorescence of the tdTomato and KRT20 as a differentiation marker by immunostaining.

In FIG. 5 (a), "+Vehicle" indicates the result of the control mouse to which the solvent was administered alone. In FIG. 5 (b), "+Dimerizer" indicates the result of the mouse to which the AP20187 was administered. In FIGS. 5(a) and 5(b), a scale bar indicates 100 µm.

As a result, as shown in FIG. 5 (b), it was clear that the administration of the AP20187 induced apoptosis, and the LGR5-positive cancer stem cell completely died. On the other hand, the LGR5-negative cell remained intact.

Figure 6:
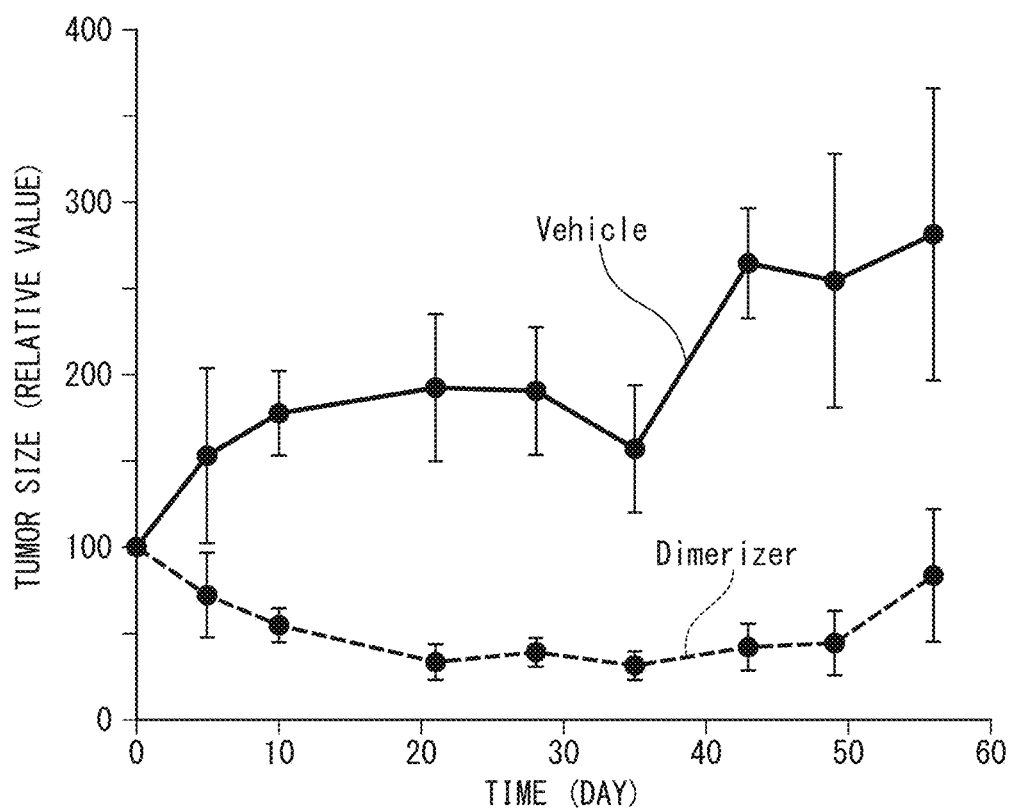
FIG. 6 is a graph showing a result obtained by measuring the size of a tumor of each of a mouse (Dimerizer) to which AP20187 is administered and a control mouse (Vehicle), regularly.

In addition, FIG. 6 is a graph showing a result obtained by measuring the size of a tumor of each of a mouse (Dimerizer) to which the AP20187 is administered and the control mouse (Vehicle), regularly. As a result, it was confirmed that the tumor size was reduced by the administration of the AP20187. Eventually, however, it was clear that the tumor size increased again.

In addition, the inventors examined the expression of the LGR5 gene in the tumor tissue after the administration of the AP20187. As a result, it was clear that the expression of the LGR5 gene once disappeared was recognized again. In addition, it was also clear that a re-increase of the tumor size corresponds to re-expression of the LGR5 gene.

From the above results, it was clear that the LGR5-positive cancer stem cell is involved in tumor growth and the LGR5-negative cancer cell has an ability to dedifferentiate into the LGR5-positive cancer stem cell. From this cancer stem cell treatment model using the AP20187 according to the present experimental example, it became clear that short-term treatment using a single drug targeting only the cancer stem cell causes tumor recurrence. Furthermore, it was revealed that continuous cancer stem cell treatment could suppress tumor growth, although the tumor was not completely +cured.

Experimental Example 5

(Examination of Combined Model of Cancer Stem Cell-specific Anticancer Drug and Anticancer Drug)

In the tumor prepared by the xenograft of the LGR5-iCT organoid prepared in Experimental Example 4, the AP20187 is a hypothetical cancer stem cell-specific anticancer drug. Thus, the effect of cancer treatment by combining AP20187 with existing anticancer drugs were examined.

Specifically, the LGR5-iCT organoid prepared in Experimental Example 4 was xenografted under the renal capsule of NOG mice (7-12 weeks old, male) by the same method as Experimental Example 2. Two clones of clone CCO7 and clone CCO25 were used as the LGR5-iCT organoids.

Subsequently, after a tumor was formed, the existing anticancer drug was administered to mice. As an existing anticancer drug, Cetuximab (CTX), which is an anti-EGF receptor antibody, was used. Cetuximab was administered twice at the start of drug administration (day 0) and on the 7th day. In addition, only the solvent instead of Cetuximab was administered to the control mice.

Thereafter, AP20187 was administered daily for 5 days from the 8th day to the 12th day after the start of the Cetuximab administration to the mice. In addition, for comparison, a control mice were used to which only the solvent was administered daily for 5 days from the 8th day to the 12th day after the Cetuximab administration to the mice.

Figure 7:
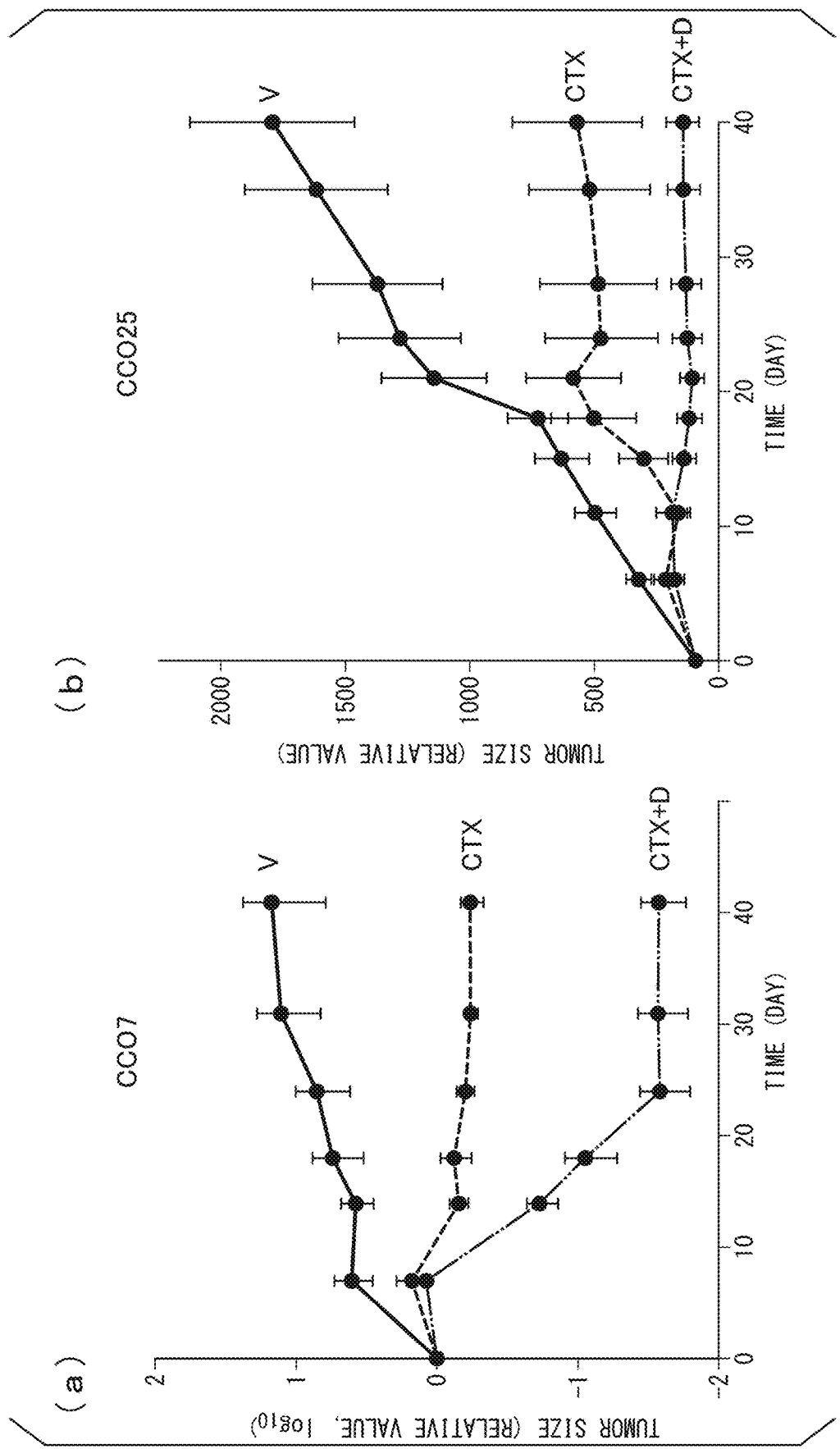
FIGS. 7(a) and 7(b) show graphs of a result obtained by measuring the size of tumor tissue derived from an organoid regularly, in Experimental Example 5.

Subsequently, the tumor size of each mouse was measured regularly. FIGS. 7(a) and 7(b) show graphs of a result obtained by measuring the tumor size regularly. FIG. 7(a) shows the result of the tumor derived from the clone CCO7 of the LGR5-iCT organoid, and FIG. 7(b) shows the result of the tumor derived from the clone CCO25 of the LGR5-iCT organoid.

In FIGS. 7(a) and 7(b), "V" indicates the result of the control mouse, "CTX" indicates the result of the mouse to which Cetuximab and the solvent were administered, and "CTX+D" indicates the result obtained by administering Cetuximab and AP20187.

As a result, it was clear that even when using any organoid clone, the tumor size was significantly reduced by administering Cetuximab and AP20187 in combination. In addition, more than 95% tumor reduction was observed in 5 out of 6 mice transplanted With CCO7 clones, to which Cetuximab and AP20187 were administered in combination, and in 5 out of 14 mice transplanted with CCO25 clones, it was observed that the cancer tissues completely disappeared.

The above results indicate that the combined use of a cancer stem cell-specific anticancer drug and an existing anticancer drug is effective for cancer treatment. In addition, it is considered that a drug with a concomitant effect varies depending on the cancer, and the concomitant effect can be predicted from an expression level of LGR5 by the drug.

Experimental Example 6

(Examination of Effectiveness of Anticancer Drug against Cancer Stem Cell and Cancer Cell)

A CMV-GFP construct was further introduced into the LGR5-iCT organoid prepared in Experimental Example 4. In the CMV-GFP construct, a GFP gene was linked downstream of the CMV promoter, which is the forced expression promoter. Therefore, regardless of whether or not the LGR5 gene was expressed, the GFP gene was expressed in all cells and emitted fluorescence of the GFP protein. Hereinafter, these organoids may be referred to as "LGR5-iCT/CMV-GFP organoids" in some cases.

In the LGR5-iCT/CMV-GFP organoid, survival activity of the cancer cell can be observed by fluorescence of GFP, and survival activity of the cancer stem cell can be observed by fluorescence of tdTomato.

Using the LGR5-iCT/CMV-GFP organoid, high-throughput screening of existing anticancer drugs used for the treatment of colon cancer was performed, and the effects on the cancer cells and the cancer stem cells were examined.

Figure 8:
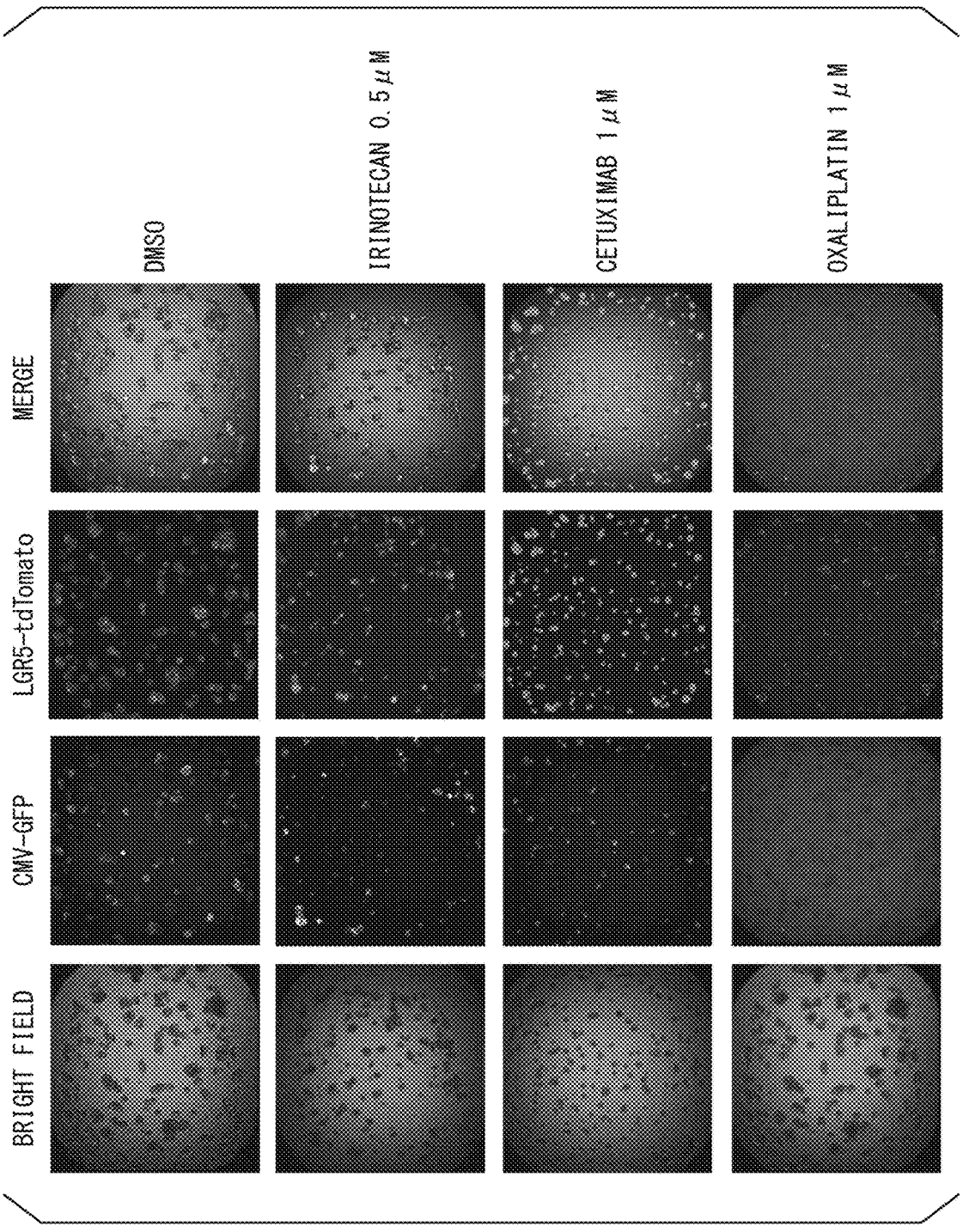
FIG. 8 is a micrograph of an organoid, showing a typical result of Experimental Example 6.

FIG. 8 is a micrograph of an organoid showing a typical result. In FIG. 8, "BRIGHT FIELD" indicates a bright field observation image. "CMV-GFP" indicates a fluorescence micrograph obtained by observing GFP fluorescence". "LGR5-tdTomato" indicates a fluorescence micrograph obtained by observing tdTomato fluorescence. "Merge" indicates the result obtained by synthesizing the bright-field observation image, the GFP fluorescence micrograph, and the micrograph of tdTomato fluorescence. In addition, Irinotecan, Cetuximab, and Oxaliplatin are existing anticancer drugs. Each anticancer drug was added to an organoid medium at the final concentration shown in FIG. 8. In addition, "DMSO" refers to dimethyl sulfoxide added to the medium instead of the anticancer drug as a control.

As a result, irinotecan showed a growth suppression effect against the cancer cell, but was not effective against the cancer stem cell. In addition, it was clear that Cetuximab as an anti-EGFR antibody significantly increases the survival activity of cancer stem cells. In addition, it was clear that oxaliplatin kills both cancer stem cells and cancer cells.

These findings demonstrate that the method of the present Experimental Example can be used for screening an anticancer drug or the like effective against cancer stem cells.

INDUSTRIAL APPLICABILITY

According to the present invention, it is possible to provide a technique of performing gene locus-specific gene manipulation on a tissue stem cell.

The invention claimed is:

1. A human tissue stem cell in which a gene of interest is introduced into a gene locus of a stem cell marker gene,
    wherein the stem cell marker gene is a Leucine-Rich Repeat-Containing G Protein-Coupled Receptor 5 (LGR5) gene and
    wherein the gene of interest is introduced into exon 18 of an LGR5 gene locus.

2. The human tissue stem cell according to claim 1, wherein the gene of interest is a reporter gene.

3. The human tissue stem cell according to claim 1, wherein the gene of interest is a first reporter gene, and a second reporter gene that is operated by a forced expression promoter is further introduced.

4. The human tissue stem cell according to claim 1, which is a stem cell derived from cancer tissue.

* * * * *